United States Patent
Jin et al.

(10) Patent No.: US 8,692,559 B2
(45) Date of Patent: Apr. 8, 2014

(54) CONNECTOR SLEEVE FOR A LEAD OF AN INTERNAL PULSE GENERATOR

(75) Inventors: Li Jin, Cupertino, CA (US); Hanson Chang, Arcadia, CA (US); Keith Victorine, Santa Clarita, CA (US); Tyler Strang, Valencia, CA (US); Armando M. Cappa, Granada Hills, CA (US)

(73) Assignee: Pacesetter, Inc., Sylmar, CA (US)

( * ) Notice: Subject to any disclaimer, the term of this patent is extended or adjusted under 35 U.S.C. 154(b) by 214 days.

(21) Appl. No.: 13/188,116

(22) Filed: Jul. 21, 2011

(65) Prior Publication Data

US 2013/0021040 A1 Jan. 24, 2013

(51) Int. Cl.
*A61B 5/05* (2006.01)
*A61N 1/00* (2006.01)
*H01R 24/00* (2011.01)
*H01R 27/00* (2006.01)
*A61B 17/00* (2006.01)
*G01R 5/00* (2006.01)
*G01R 13/00* (2006.01)
*A61N 1/05* (2006.01)

(52) U.S. Cl.
USPC ............ 324/538; 600/423; 607/37; 439/626; 439/218

(58) Field of Classification Search
CPC .......... A61B 17/00; G01R 5/00; G01R 13/00; A61N 1/05
USPC .................. 324/538; 439/626, 218; 600/423; 607/37
See application file for complete search history.

(56) References Cited

U.S. PATENT DOCUMENTS

| | | | |
|---|---|---|---|
| 7,633,023 B1 | 12/2009 | Cappa et al. | |
| 7,777,140 B2 | 8/2010 | Cappa et al. | |
| 7,917,228 B2 | 3/2011 | Wenger | |
| 2004/0230267 A1 * | 11/2004 | Wenger | 607/116 |
| 2010/0048062 A1 * | 2/2010 | Cappa et al. | 439/626 |
| 2012/0019260 A1 * | 1/2012 | Reddy et al. | 324/543 |

FOREIGN PATENT DOCUMENTS

| | | |
|---|---|---|
| WO | 2004101063 A1 | 11/2004 |
| WO | 2005077453 A2 | 8/2005 |
| WO | 2005077453 A3 | 11/2005 |
| WO | 2005077453 A3 | 1/2006 |

\* cited by examiner

*Primary Examiner* — Melissa Koval
*Assistant Examiner* — Farhana Hoque

(57) ABSTRACT

An interface device provides one or more electrical connection points disposed on a connector sleeve. The connection points provide electrical communication between a lead connector end of an implantable medical lead and one or more leads of a testing device in such a manner as to minimize potential damage to the lead connector end.

26 Claims, 9 Drawing Sheets

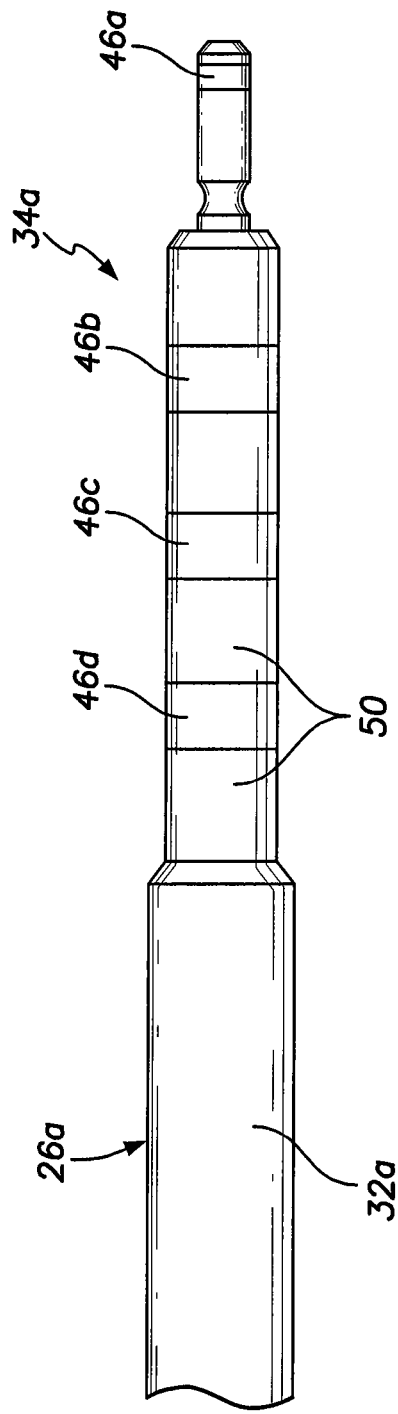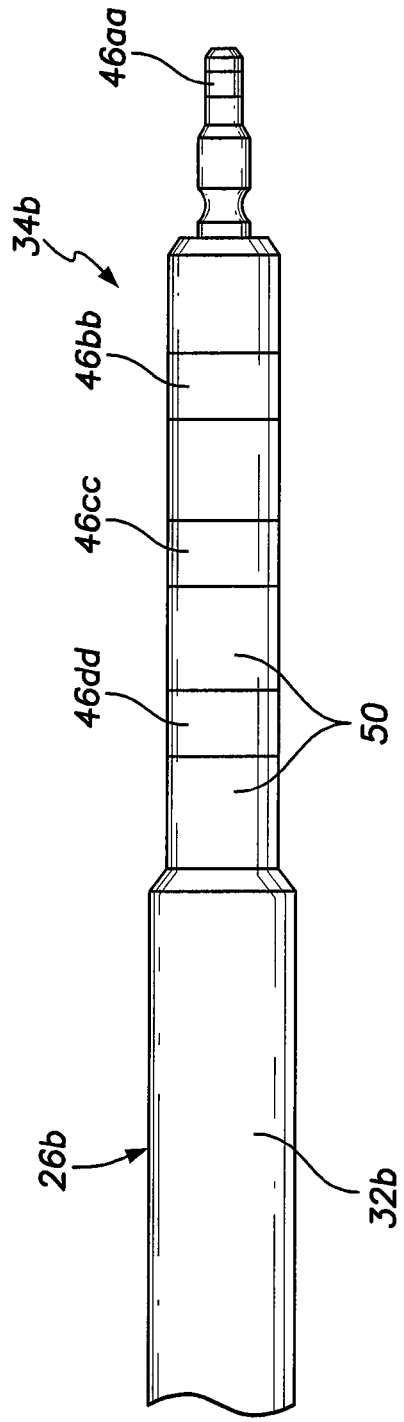
FIG. 2A PRIOR ART
FIG. 2B PRIOR ART

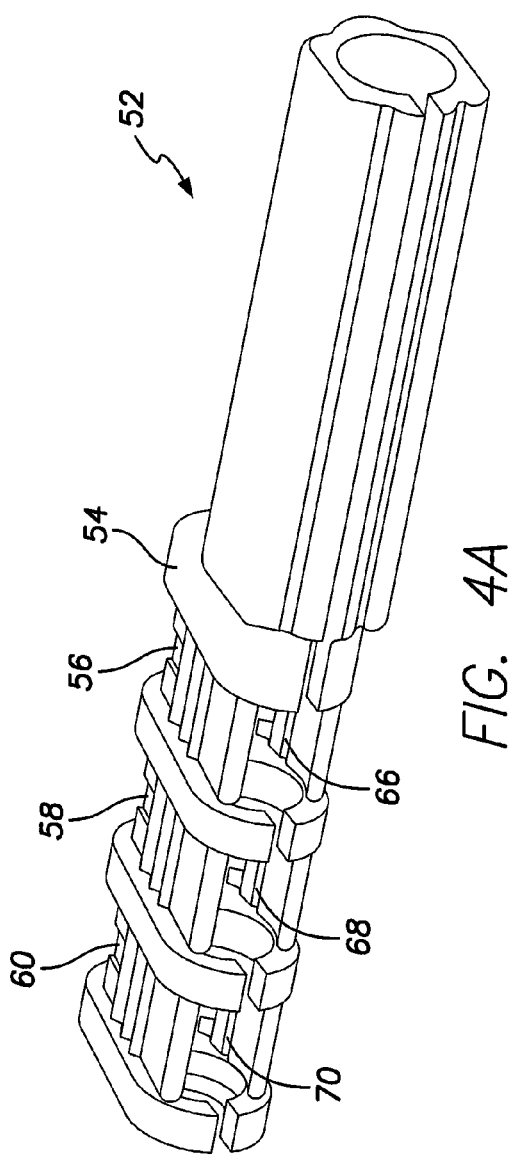
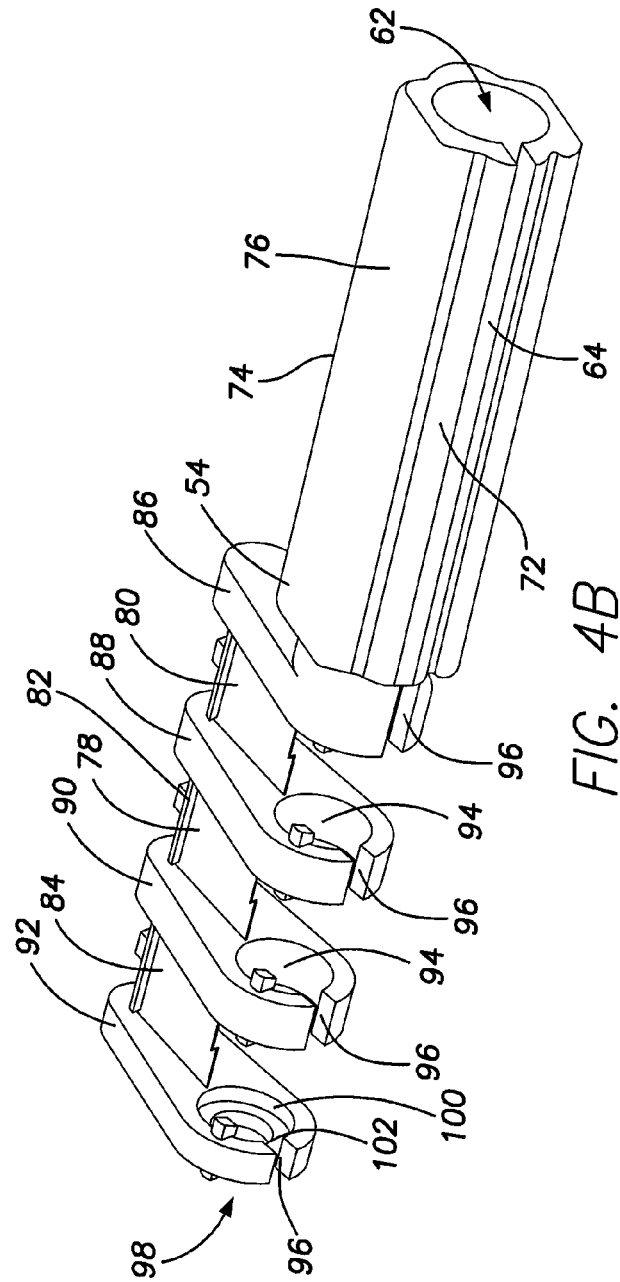
FIG. 4A
FIG. 4B

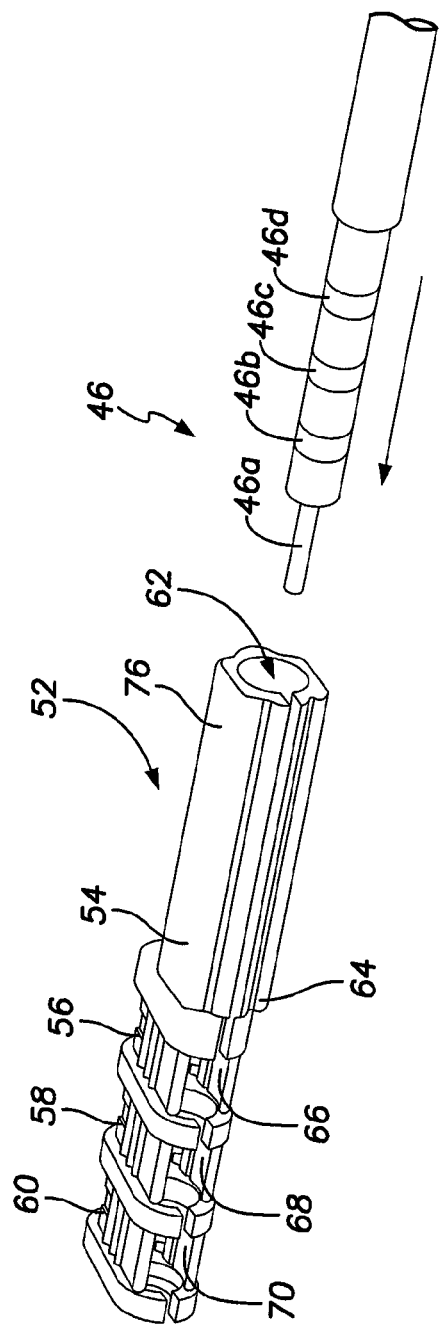
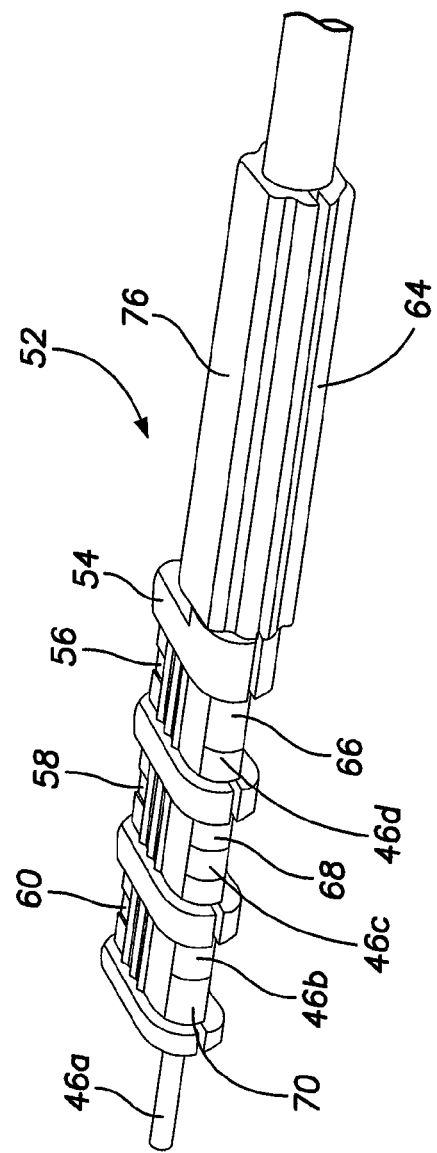

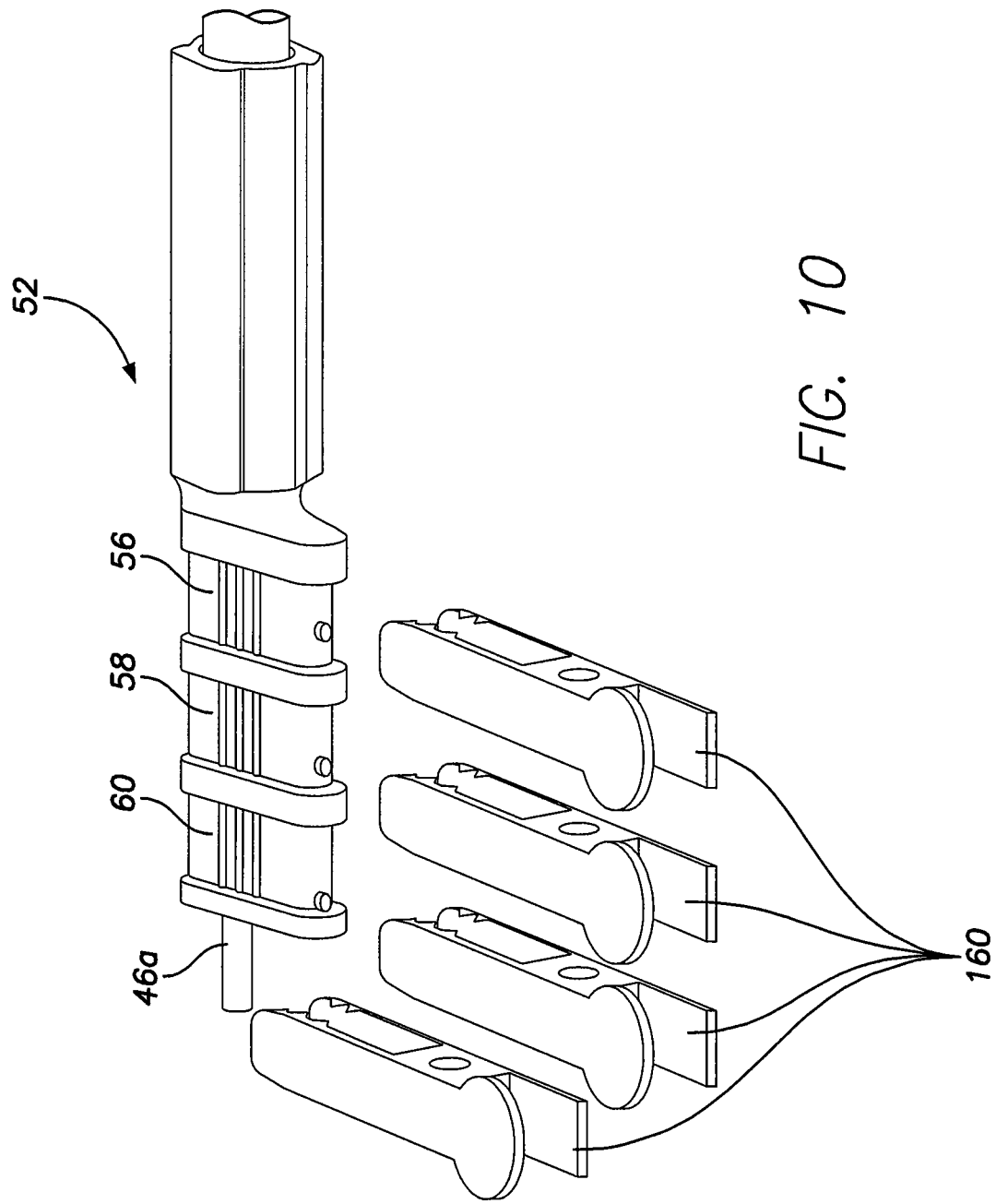

CONNECTOR SLEEVE FOR A LEAD OF AN INTERNAL PULSE GENERATOR

FIELD OF THE INVENTION

Aspects of the present invention relate to medical apparatus and methods. More specifically, the present invention relates to devices for connecting a lead connector end of an implantable medical lead to a testing device.

BACKGROUND OF THE INVENTION

An internal pulse generator ("IPG") such as an artificial pacemaker or implantable cardioverter defibrillator ("ICD") is a medical device which uses electrical impulses to regulate the beating of a heart. In general, the pulse generator administers electrical impulses to the appropriate heart tissue via one or more leads inserted transvenously with distal ends of the leads located within the chamber or chambers of the heart. The distal ends of the leads generally support electrodes for sensing, pacing and defibrillation.

The implanted leads of the IPG typically include a conductor (or distal) end in contact with the heart and a terminal (or proximal) end connected with the pulse generator. The proximal lead connector end typically includes one or more exposed contacts electrically connected with the distal conductor end to provide the electrical pulses to the heart. To ensure proper placement of the distal conductor end within the heart, readings of the electrical conduction of the lead may occur at the proximal lead connector end through a testing device, such as a Pacing System Analyzer (PSA). During testing, the PSA may be connected to one or more contacts of the lead at the proximal connector end to test for proper function and connection of the distal end to the heart. Prior standards for implanted leads, such as IS-1 standard leads, include two conductors with exposed contacts at the proximal lead connector end that the PSA electrically connects with to test the lead placement. Other standards, such as IS4, include more than two conductors, but are tested in a similar manner by the PSA.

To test the electrical connections of the lead, an operator places one or more alligator or similar spring loaded clips onto the lead connector end in direct contact with the contacts of the lead connector end. However, such clips may not be satisfactory for use with some leads as the contacts of the proximal lead connector end may be too densely situated on the lead end. For example, the clips might come into contact with each other on the lead connector end, which would provide inaccurate PSA testing results. Also, placement of clips directly onto the lead connector end may cause undesirable deformation of the surface of the connector end, in some instances resulting in the tearing of the seals of the connector end.

There is need in the art for a device for, and method of, electrically coupling a PSA to a lead connector end of an implanted lead that overcomes the aforementioned issues.

BRIEF SUMMARY OF THE INVENTION

One implementation of the present disclosure may take the form of an adapter for testing an implantable medical lead with a testing device and a cable arrangement in communication with the testing device and terminating in pinching clips, wherein the implantable medical lead includes a lead connector end with ring contacts. In one embodiment, the adapter includes a housing, conductive clips and insulating walls. The housing includes a handle portion, a connector interface portion and a bore through the handle portion and the connector interface portion configured to receive the lead connector end of the implantable medical lead. The conductive clips are disposed in respective recesses in the connector interface portion of the housing. The conductive clips are configured to electrically connect to the ring contacts of the lead connector end of the implantable medical lead when the lead connector end is positioned within the bore of the housing. The insulating walls are disposed on the connector interface portion of the housing between the adjacent conductive clips. The insulating walls are configured to prevent electrical communication between the conductive clips. Each conductive clip provides an electrical connection point for the respective pinching clip of the cable arrangement.

Another implementation of the present disclosure may take the form of a connector interface device for connecting a testing cable to a lead connector end of an implantable medical lead, the lead connector end including ring contacts and the testing cable terminating in pinching clips. In one embodiment, the connector interface device includes a housing, a bore and a conductor member, such as, for example, u-shaped conductive clip. The housing includes a handle portion and conductor positions, such as, for example, conductor recesses. The bore extends through the handle portion of the housing and is configured to receive the lead connector end of the implantable medical lead. A conductor member, such as, for example, a u-shaped conductive clip, is disposed at each conductor position, such as, for example, a conductor recess. Each conductor member, such as, for example, a conductive clip, is configured to electrically connect to a respective ring contact on the lead connector end when the lead connector end is positioned within the bore.

Yet another implementation of the present disclosure may take the form of a method for testing placement of a distal end of an implantable medical lead within a patient. In one embodiment, the method includes: positioning the distal end of the implantable medical lead at a heart location of the patient; inserting the lead connector end into a connector interface sleeve, the connector interface sleeve configured to provide electrical connection points for a testing cable in communication with a testing device for testing the placement of the distal end of the lead; and connecting the testing cable to the connector interface sleeve at the electrical connection points, each electrical connection point of the connector interface sleeve corresponding to a single respective contact ring of the lead connector end.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIG. 2A is side view of an industry standard IS4 lead connector end with four conductors.

FIG. 2B is side view of an industry standard DF4 lead connector end with four conductors.

FIG. 4A is a front isometric view of a connector sleeve providing an interface between the alligator clips of a PSA testing cable and the conductors of a lead connector end.

FIG. 4B is a front isometric view of the housing portion of the connector sleeve of FIG. 4A with the conductive clips removed.

FIG. 8A is a front isometric view of the connector sleeve and a lead connector illustrating insertion of the lead into the sleeve.

FIG. 8B is a front isometric view of the connector sleeve and lead connector end illustrating full insertion of the lead connector end into the connector sleeve.

FIG. 10 is a rear isometric view of the connector sleeve with a fully inserted lead connector end and several alligator clips of a PSA cable for electrically connecting to the connector sleeve.

DETAILED DESCRIPTION

Implementations of the present disclosure involve an internal pulse generator ("IPG") for administering electrotherapy via an implantable medical lead having a lead connector end on a proximal end. In addition, implementations involve testing of the medical lead at the proximal lead connector end to ensure proper placement of the lead, and an interface device for facilitating the connection of the proximal lead connector end to a testing device.

Before a detailed discussion of the connector sleeve interface assembly is provided, a general discussion is first given regarding common features for testing a lead of an implantable medical device at the proximal end of the lead, including common features of a multi-pole lead, such as, for example, an IS4 or DF4 type lead of an IPG.

Figure 1:
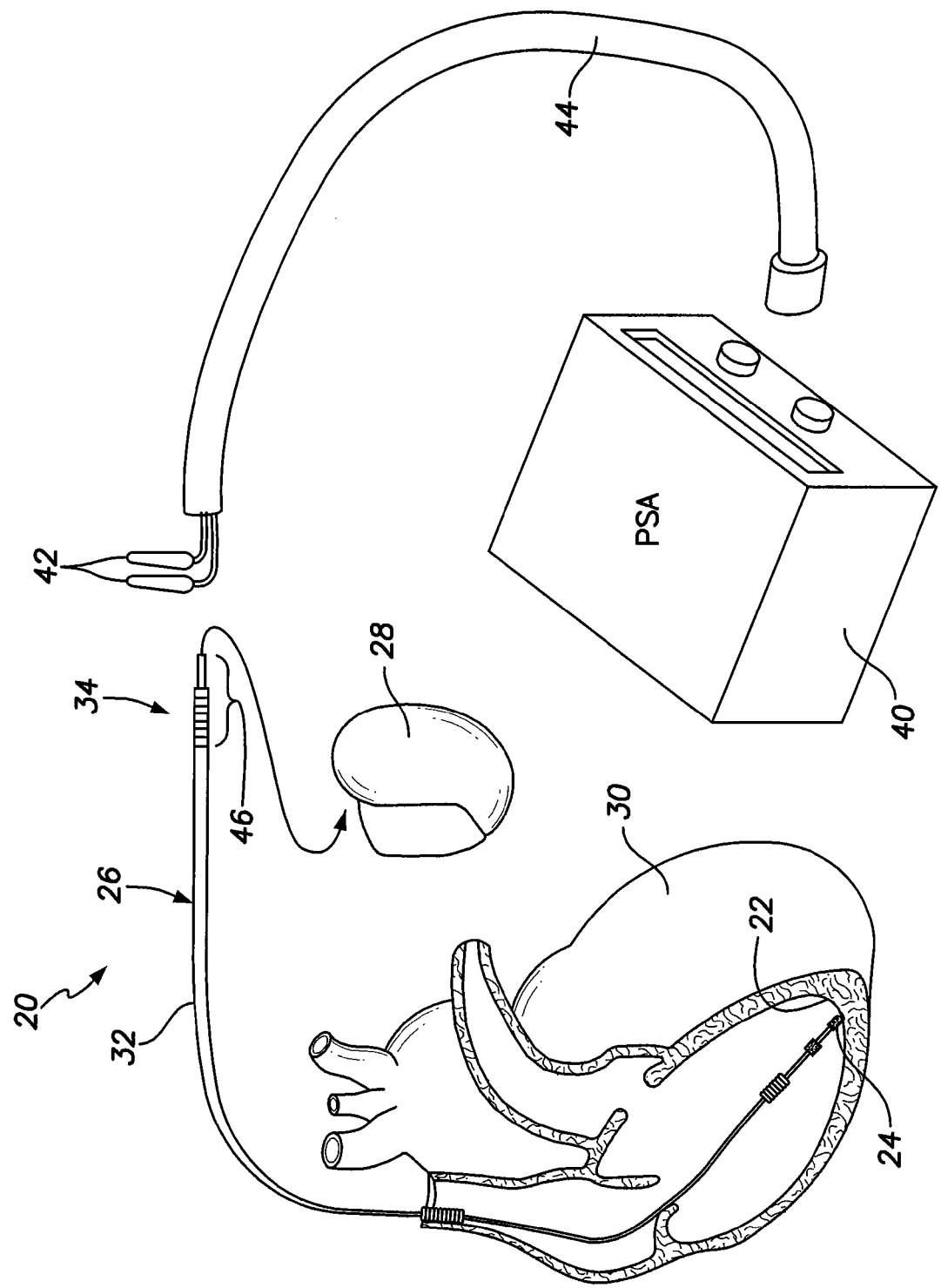
FIG. 1 is a perspective view of a system for testing the placement of a lead of an implantable medical device within a heart.

FIG. 1 illustrates a system 20 for determining the efficacy of a body tissue site 22 chosen for an electrode 24 at a distal end of a lead 26 intended for connecting an IPG 28 to the body tissue. The system 20 incorporates an IPG 28 such as a pacemaker or cardioverter-defibrillator (ICD) providing electrical stimulation to a heart 30. The lead 26 may include an insulating sheath 32 interconnecting the electrode 24 appropriately secured to the interior wall of the heart at the body tissue site 22 and an electrical connector 34 at a proximal end 46 to which can be attached the electrical stimulation device 28.

As discussed above, it may sometimes be necessary for an attending physician to verify that the body tissue site 22 selected for the implantation procedure is appropriate and will provide the desired result. For this reason, a PSA (Pacing System Analyzer) 40 may be electrically connected to the lead 26 at the proximal lead connector end 46 to verify the proper placement of the lead. In short, the PSA 40 is an external testing and measuring device which, for example, can pace the heart during the implantation procedure and can measure stimulation thresholds, sensing thresholds, and lead impedance. The PSA 40 may also be used to test pulse generator function prior to implant, measure slew rate or print an electrogram of a sensed R-wave.

In order to use the PSA 40 in connection with the lead 26, it is necessary to connect the electrical connector 34 of the lead 26 to the PSA cable 44. Many PSA devices 40 utilize alligator clips 42 or a similar connecting device to connect the PSA to the lead connector end 46 of the lead 26. However, as noted above, such clips 42 can damage the lead connector end 34 or provide an unreliable electrical signal to the PSA for analysis, especially in leads with several electrical terminals on the lead connector end.

Leads of an IPG apparatus generally include a standard design that allows for interchangeability between leads and IPGs from different manufacturers. Examples of such standard designs include the IS4 standard and the DF4 standard, both of which provide for a four-pole connector system for IPGs. An 184 standard lead connector end is illustrated in FIG. 2A as a low-voltage connector 34A. A DF4 standard is illustrated in FIG. 2B as a combined high and low-voltage connector 34B. The differing connectors may provide varied electrical pulses from the IPG to treat different ailments. The IS4 and DF4 design standards are provided as examples of multi-pole lead connector end designs that may be employed with the connector sleeve 52 discussed below with respect to FIGS. 4A through 10. While discussed herein in the context of connecting with IS4 and DF4 lead connector ends, the concepts discussed herein with respect to the connector sleeve 52 of FIGS. 4A through 10 are readily applicable to such connector sleeves 52 connecting with all types of multi-pole lead connector ends.

As seen in FIG. 2A, the first connector 34A includes a plurality of proximal contacts, namely, a straight pin tip contact 46A, and three ring contacts 46B, 46C, and 46D, respectfully, as one advances in a distal direction. Each of the contacts 46A, 46B, 46C, and 46D is of a low voltage design and is separated from its neighbor by a sealing surface 50. In this instance, the lead is designated 26A and the insulating sheath is designated 32A. Similarly, as seen in FIG. 2B, the second connector 34B includes a plurality of proximal contacts, namely, a stepped pin tip contact 46AA, and three ring contacts 46BB, 46CC, and 46DD, respectfully, as one advances in a distal direction. The contacts 46AA and 46BB are of low voltage design and each contact is separated from its neighbor by a sealing surface 50 while the contacts 46CC and 46DD are of high voltage design and are similarly separated from their neighbors by sealing surfaces 50. In this instance, the lead is designated 26B and the insulating sheath is designated 32B. In general, the particular information obtained from each contact depends on the lead placement and the information being sought by the physician.

Figure 3:
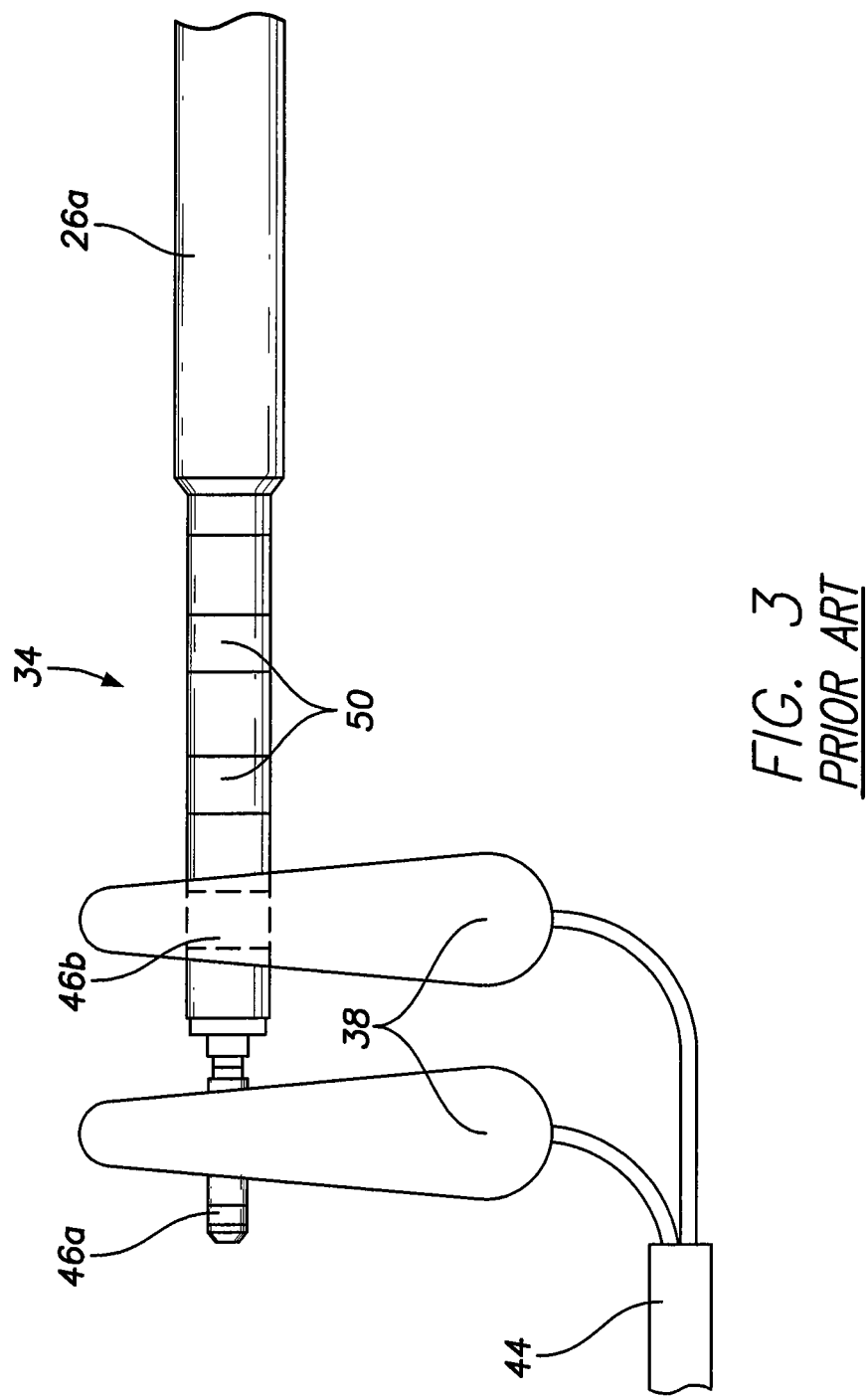
FIG. 3 is a side view of the lead connector end of FIG. 2A with a plurality of alligator clips of a PSA testing cable attached to two of the conductors of the lead connector end.

FIG. 3 is a quad contact lead connector end 34 (such as lead connector 34A of FIG. 2A) with PSA cable 44 connected to pin tip contact 46A and ring contact 46B by spring clips 38 for testing. As shown, many spring clips 38 that provide an interface to the PSA may be too large for the ring contacts of the lead connector end 34. Thus, in some situations, the spring clips 38 may contact each other or may not properly contact the pin contact 46B, which would provide inaccurate PSA testing results. Also, placement of clips 38 directly onto the lead connector end 34 may cause undesirable deformation of the surface of the connector end, including tearing of the seals 50 of the connector end adjacent to the ring contacts. It is therefore desirable to have an adapter to interface a PSA cable with a lead connector end 34 to permit use of PSA for testing the IPG leads.

It should be noted that the adapters and cables described below are not intended for implantation within a patient's body but are for testing the leads following positioning of the distal end electrode 24 adjacent or within the patient's heart. Once testing has been completed, the adapter and testing cables are removed from lead connector end 34 and lead 26 is connected to IPG 28 via insertion of the lead connector end 34 into the IPG 28.

FIGS. 4A through 10 illustrate a connector sleeve 52 for a lead connector of an implantable medical device that provides an interface between the ring contacts of the proximal lead connector end and the spring clips of a PSA cable. In general, the sleeve 52 includes a housing 54 and one or more conductive clips 56-60 that provide an electrical connection between the teeth of the alligator clips of the PSA cable and the ring contacts of the lead connector end. To test the lead with the PSA, an operator inserts the lead connector end into the sleeve, aligning each ring contact of the lead connector end with its respective conductor clip 56-60 of the sleeve 52. The operator then attaches each alligator clip of the PSA cable to the outer surface of the respective conductive clip 56-60 to test the electrical connections of the lead placement. The features of the connector sleeve 52 will now be explained in more detail.

FIG. 4A is a front isometric view of a connector sleeve 52 providing an interface between the alligator clips of a PSA testing cable and the conductors of an lead connector end. As mentioned above, the sleeve 52 generally includes a plastic housing 54 and one or more conductive clips 56-60. The plastic housing 54 can best be seen in FIG. 4B, which is a front isometric view of the housing of the connector sleeve of FIG. 4A with the conductive clips removed. The housing 54 includes a handle portion 76 and a connector interface portion 78. The handle portion 76 is generally rectangular in shape with a front side 72 and a back side 74. A circular bore 62 is provided through the handle portion 76 oriented generally parallel to the front side 72 and back side 74 of the handle. In general, the diameter of the bore 62 is sufficient to allow for the insertion of a lead of an IPG into the bore, as described in more detail below with reference to FIGS. 8A-10. In addition, a slit opening 64 is provided along the front side 72 of the housing 76 and, as described in more detail below, generally aligns with one or more viewing aperture 66-70 of the conductive clips 56-60 of the connector sleeve. The width of the slit opening 64 may be sufficient to prevent the lead of the IPG from passing through the slit, but allow a guide wire or stylet to pass through the slit without disturbing the position of the lead distal end in the patient.

The connector interface portion 78 of the housing 54 is located adjacent the handle portion 76 at the distal end of the bore 62 and provides for one or more contact clip recesses 80-84 within the housing in which are seated the conductive clips of the sleeve 52. The particular embodiment shown in FIG. 4B includes three such clip recesses, a proximal clip recess 80, a middle clip recess 82 and a distal clip recess 84. In other embodiments, however, the connector sleeve may include any number of clip recesses for retaining the conductive clips within the housing. Between each clip recess 80-84 of the connector interface portion 78 of the housing 54 is an insulating wall 86-92 configured to maintain the conductive clip within the respective recess of the housing and to insulate each conducting clip from its neighbor clip. For example, in the embodiment of FIG. 4B, the proximal recess 80 is between insulating walls 86 and 88, the middle clip recess 82 is between insulating walls 88 and 90, and the distal recess 84 is between insulating walls 90 and 92. The insulating walls 86-92 partially define the width of each clip recess 80-84 as well as electrically isolate the conductive clips from each other. In addition, each insulating wall 86-92 of the housing 58 includes a bore 94 having different dimensions from the bore 62 of the handle portion 76 of the housing 54. For example, the bores 94 are adapted to receive the lead connector end, while the bore 62 is adapted to receive the lead boot. The bores 94 of the insulating walls are axially aligned with the handle bore 62 such that a lead connector end inserted into the housing may pass through each bore of the housing. The insertion of the lead connector end into the bores of the housing is described in more detail below with reference to FIGS. 8A-10. Each insulating wall 86-92 may also include a slit opening 96 of similar dimensions as the slit opening 64 of the handle portion 76 of the housing 54. The slit openings 96 of the insulating walls 86-92 are axially aligned with the handle slit opening 64 to allow a guide wire or stylet to pass through the slit without disturbing the lead distal end.

In one embodiment, the insulating wall 92 located at the distal end of the housing may include a stepped bore 98 with at least two inner diameters. For example, the stepped bore 98 may include a first circumferential surface 100 of a first diameter with similar dimensions as the bore 92 of the insulating walls. The stepped bore may also include a second circumferential surface 102 with a second inner diameter 102, with the second inner circumference being smaller the first inner circumference. The stepped bore 98 of insulating wall 92 may generally conform to the stepped structure of the proximal end of the lead connector end, as shown in FIGS. 2A and 2B, to allow the pin contact 46A to pass through the stepped bore 98 while retaining the rest of the lead connector end 34A within the housing 54. In addition, the stepped bore 98 may prevent an inserted lead from distally over-extending through the connector sleeve and, as a result, assuring the ring conductors on the lead connector end are aligned with the conductive clips, as explained in more detail below.

By allowing the pin contact 46A to be exposed when the lead is inserted into the connector sleeve, shown in FIG. 8B, an alligator clip may be attached to the pin contact. Also, a helix extension/retraction tool can be attached to the pin contact without having to remove the connector sleeve.

In general, the housing structure 54 of the connector sleeve 52 is injection molded using a plastic material such as polysulfone or the like. However, the housing 54 may be constructed from any type of plastic in any manner known or hereafter developed for molding plastic.

Returning to FIG. 4A, the connector sleeve 52 also includes one or more conductive clips 56-60 seated in the corresponding clip recesses 80-84 of the connector interface portion 78 of the housing 54. For example, the connector sleeve 52 of FIG. 4A includes three conductive clips, a proximal conductive clip 56 seated in the proximal clip recess 80, a middle conductive clip 58 seated in the middle clip recess 82 and a distal conductive clip 60 seated in the distal clip recess 84. The conductive clips 56-60 are generally u-shaped clips constructed from a conductive metal, such as stainless steel, titanium, MP35N or other electrically conductive materials. The conductive clips 56-60 are oriented within the clip recesses 80-84 of the housing 54 such that the opening 66-70 of each clip 56-60 is aligned with the front 72 of the housing. In addition and explained in more detail below, the openings 66-70 of the clips 56-60 also provide a viewing aperture into the clips so that the alignment of the ring contacts of the IPG lead within the clips can be visually verified when the lead is inserted into the connector sleeve 52. The conductive clips 56-60 of the sleeve 52 are maintained within the corresponding clip recesses of the housing through one or more bossing features of the housing, described in more detail below.

Figure 5:
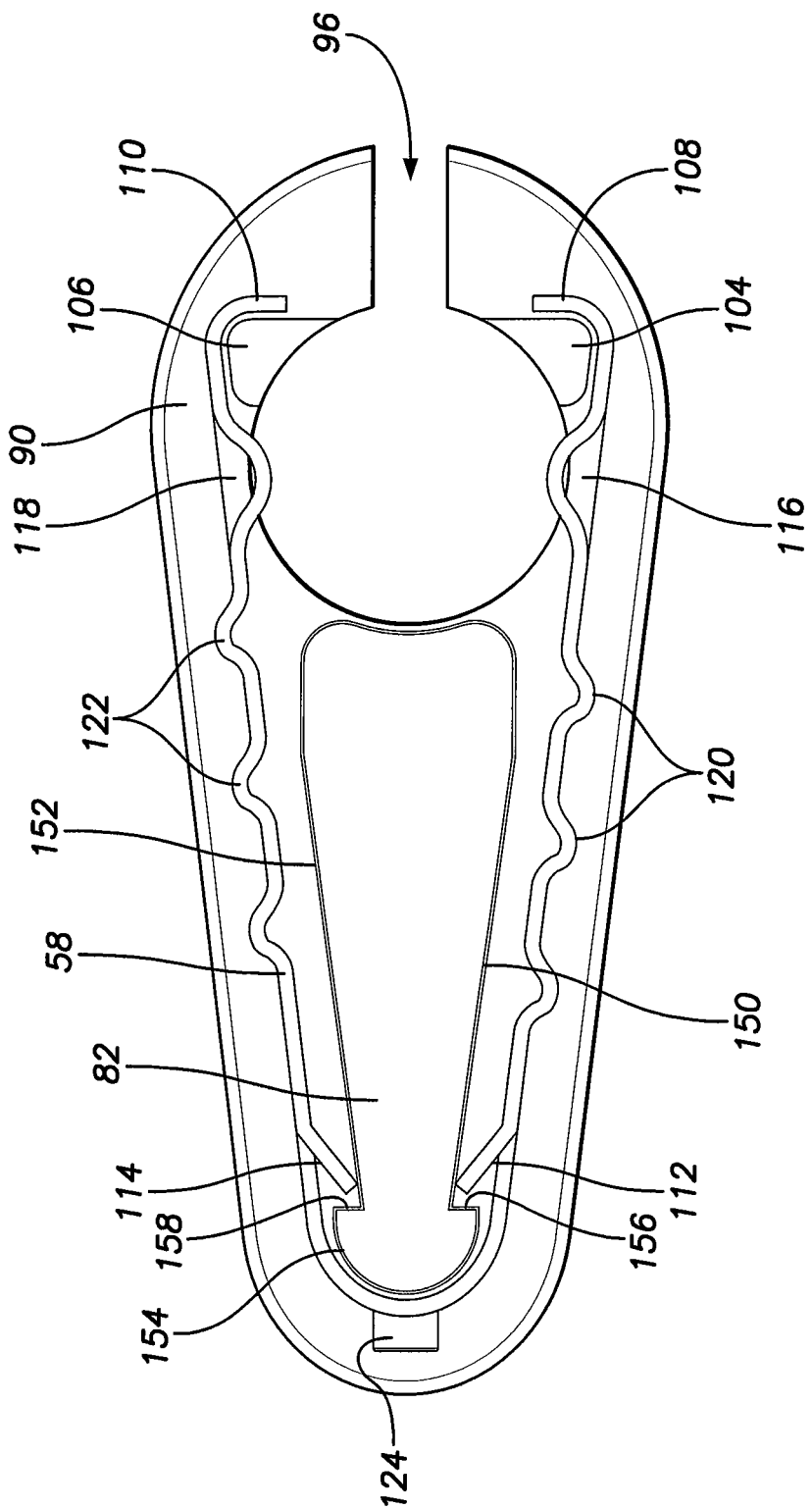
FIG. 5 is a transverse cross-sectional view of the connector sleeve illustrating a conductive clip and housing as taken along section line 5-5 of FIG. 6.
Figure 6:
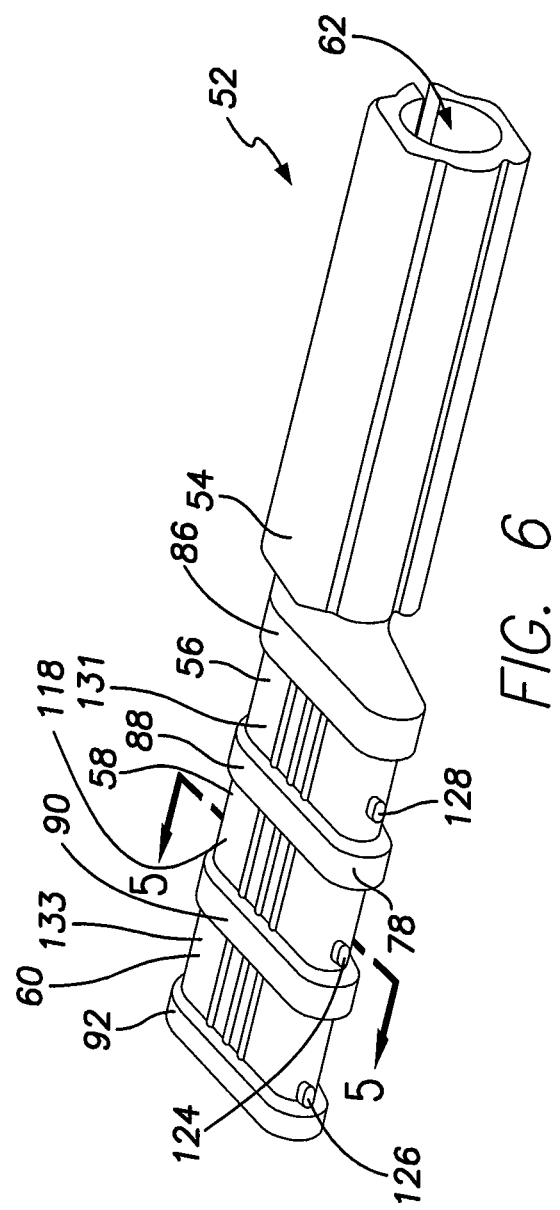
FIG. 6 is a rear isometric view of the connector sleeve providing an interface between the alligator clips of a PSA testing cable and the conductors of a lead connector end.

FIG. 5 is a cross-sectional view of the connector sleeve as taken along section line 5-5 of FIG. 6, illustrating a cross-section view through center dimples 116, 118 of middle conductive clip 58, a cross-sectional view of middle clip recess 82 and a side view of insulating wall 90. As shown, the clip recess 82 includes a top surface 150, a bottom surface 152 and a back surface 154. The back surface 154 includes a semi-circular surface corresponding to the circular portion of the u-shaped conductive clip 58 such that, when the clip is seated within the clip recess 82, the circular portion of the conductive clip is adjacent to the back surface 154. The clip recess 82 also includes a top clip retention notch 156 in the top surface 150 of the clip recess and a bottom clip retention notch 158 in the bottom surface 152 of the clip recess. As explained in more detail below, the top clip retention notch 156 and the bottom clip retention notch 158 accept a punch-in feature of the conductive clip 58 to retain the clip within the clip recess 82.

Although only the middle conductive clip 58 of the sleeve is illustrated in FIG. 5, each conductive clip may be similar is shape and orientation within the corresponding clip recess of the connector sleeve housing. As briefly described above, the u-shaped conductive clip 58 is oriented within the clip recess 82 such that the open portion of the clip aligns with the slit opening 96 of the insulating wall 90 and the circular portion of the clip is adjacent the back surface 154 of the clip recess. In addition, the insulating wall 90 includes a top bossing stub 104 and a bottom bossing stub 106 that protrude from the side of the insulating wall. The top bossing stub 104 is shaped to engage a top fold over feature 108 at the open end of the conductive clip 58 and the bottom bossing stub 106 is similarly shaped to engage a bottom fold over feature 110. The top and bottom fold-overs 108, 110 engage the top and bottom bossing stubs 104, 106 to retain the clip within the housing of the sleeve. The bossing features also aid in preventing the conductive clip 58 from damaging the lead connector end during engagement of the conductive clip with the lead connector end.

The conductive clip 58 also includes a top punch-in 112 feature and a bottom punch-in 114 feature that, respectively, engage the top clip retention notch 156 and the bottom clip retention notch 158 to retain the conductive clip within the housing of the sleeve. The punch-in features 112, 114 also bias the conductive clip 58 away from the clip recess surface and create a space between the conductive clip 58 and the clip recess surface such that, when an alligator clip is applied to the clip during testing, the clip may deform at least partially into the created space. More particularly, the conductive clip 58 includes a top dimple 116 and a bottom dimple 118 oriented such that, when the clip is deformed from the force of the applied alligator clip, the top dimple and the bottom dimple engage a ring conductor of the inserted lead to form an electrical connection between the conductive clip and the lead conductor. As can be understood from FIGS. 4A, 6 and 7, each of the other clips 56, 60 include similar top and bottom dimples 130, 131, 132, 133.

As should be appreciated, the top boss 104, bottom boss 106, top punch-in 112 and bottom punch-in 114 operate on the conductive clip 58 to limit the clip from pressing on the lead connector end in such a manner as to damage the lead connector end when an alligator clip is applied for testing. In general, only the top dimple 116 and the bottom dimple 118 of the conductive clip 58 contact the lead connector end when a testing alligator clip is applied to the connector sleeve. In one embodiment, when the clip 58 is free of the inward driving force of an alligator clip, the bias of the clip 58, which is outward on account of the punch-in features 112, 114, will allow the lead connector end to be inserted into the bores 94 without contacting the clips 56-58. In another embodiment, the conductive clips are configured such that there is a touch-contact to the rings, but secure electrical connection is made only when pinching clips are applied.

The conductive clip 58 also includes a set of ridges 120, 122 along the outer surface of the clip. The ridges 120, 122 interact with the teeth of the alligator clips of the PSA cable to maintain the alligator clip on the conductive clip 58 during testing of the lead of the IPG. In addition, the ridges 120 along the top of the conductive clip 58 are offset from the ridges 122 along the bottom of the clip to conform with the offset teeth of the alligator clip. The offset nature of the top ridges 120 and the bottom ridges 122 provide optimal engagement with the teeth of the alligator clip.

Figure 7:
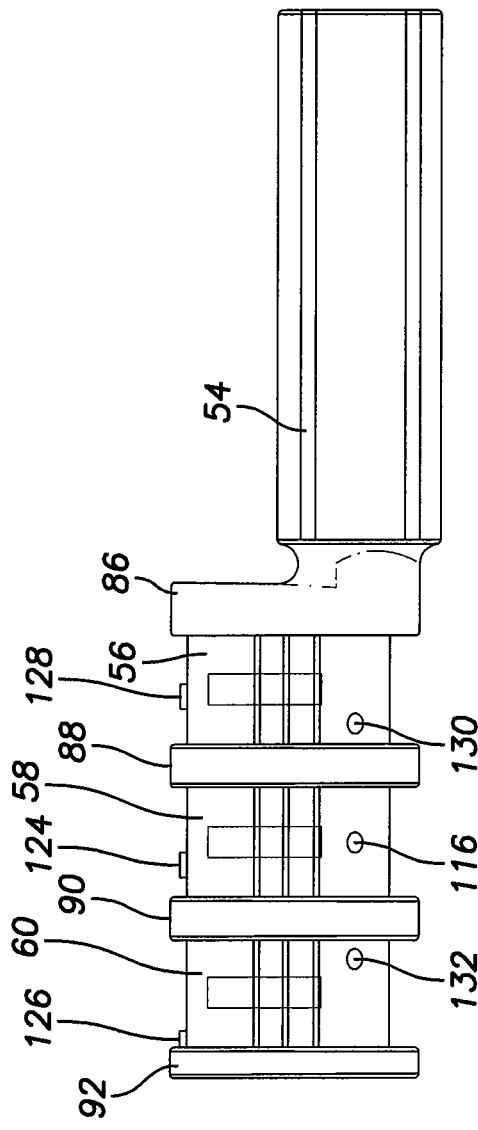
FIG. 7 is a top plane view of the connector sleeve providing an interface between the alligator clips of a PSA testing cable and the conductors of a lead connector end.

As also shown in FIG. 5, a stub 124 is included that protrudes from the back surface 154 of the clip recess generally towards the back of the sleeve. The stub 124 forms a portion of an alignment system that orients the conductive clip 58 within the clip recess and ensures proper alignment of the dimples 116, 118 of the clip with the ring contacts of the lead connector end inserted into the connector sleeve. For example, FIG. 6 is a back isometric view of the connector sleeve and FIG. 7 is a top view of the connector sleeve illustrating the alignment mechanism of the stubs of the sleeve. As shown, each clip recess of the sleeve 52 includes an alignment stub, namely a proximal alignment stub 128 of the proximal clip recess, a middle alignment stub 124 of the middle clip recess and a distal alignment stub 126 of the distal clip recess. To ensure proper alignment of the clip within the clip recess of the housing 54, each alignment stub 124-128 engages a corresponding alignment opening within the respective conductive clip. For example, as shown in FIG. 6, the proximal alignment stub 128 is located generally in the center of the proximal clip recess 80. Thus, the conductive clip 56 with a corresponding alignment opening located near the center of the clip properly fits within the recess. In addition, the middle alignment stub 124 is slightly offset from the center of the clip recess toward the distal end of the connector sleeve 52. Thus, the conductive clip 58 with the corresponding alignment opening aligned with the middle alignment stub 124 may properly fit within the middle clip recess. A similar arrangement for the distal alignment stub 126 and distal conductive clip 60 is also shown. In this manner, the corresponding conductive clips 56-60 for each clip recess may be properly placed within the recess through the engagement of the alignment opening of the conductive clips with the alignment stubs 124-128.

One advantage provided by the alignment stubs is the possibility of customizing the alignment of the contact dimples of the conductive clips with the ring contacts of the lead connector end. For example, as best seen in FIG. 7, the contact dimples 116, 130, 132 of the conductive clips 56-60 are differently located on the conductive clips. More particularly, the dimple 130 of the proximal conductive clip 56 and the dimple 132 of the distal conductive clip 60 are offset from the respective clip centers, while the dimple 116 of the middle conductive clip 58 is centered on the clip. The top contact dimples 116, 130, 132 of the conductive clips 56-60 may have this alignment to match the alignment of the conductor rings of an inserted lead connector end. A corresponding arrangement exists for the bottom dimples 118, 131, 133, as can be understood form FIG. 6. Thus, to ensure that the contact dimples 116, 130, 132 & 118, 131, 133 are properly aligned with the ring contacts of the lead connector end, the proper conductive clips 56-60 may be located within the corresponding clip recesses of the sleeve 52. This may be accomplished by the alignment mechanism of the alignment stubs 124-128 and corresponding alignment openings described above. The alignment of the contact dimples 116, 130, 132 & 118, 131, 133 with the corresponding ring contacts of the lead connector end is discussed below with reference to FIG. 9.

In one embodiment, the alignment stubs 124-128 can also be used as a heat-staking feature. For example, the stubs 124-128 can be melted down to retain the contact clip, thereby providing a redundant method of retaining the contact clips onto the housing. With this feature, the punch-ins 112, 114 and/or the fold-overs 108, 110 in the contact clip may be eliminated, or all three retention features can be used.

FIG. 8A is a front isometric view of the connector sleeve 52 and lead connector end 46 illustrating insertion of the lead connector end into the sleeve, and FIG. 8B is a front isometric view of the connector sleeve and lead connector end illustrating full insertion of the lead into the connector sleeve. To use the connector sleeve 52, an operator inserts the lead connector end 46 into the bore 62 of the housing 54 at the handle end 76 of the housing. The lead connector end 46 slides through the bore 62 until the ring contacts 46B-46D on the lead connector end are positioned below the conductive clips 56-60 of the sleeve 52, and the pin contact 468 protrudes out of the distal end of the sleeve. In one embodiment, proper alignment of the ring contacts 46B-46D with the conductive clips 56-60 may be aided by the stepped bore 98 of the rear retaining wall 92. More particularly, as shown in FIG. 8B, the stepped bore 98 of the rear retaining wall 92 may be configured such that the tip contact 46A of the lead connector end 46 extends through the second circumferential surface 102 of the stepped bore 98. However, the second circumferential surface 102 of the stepped bore 98 may be small enough to prevent any additional portion of the lead connector end 46 from passing through the bore. Thus, when the lead connector end 46 is fully seated within the connector sleeve 52, the ring contacts 46B-46D of the lead connector end may be aligned with the contact dimples 116, 118, 130, 131, 132, 133 of the conductive clips 56-60.

Figure 9:
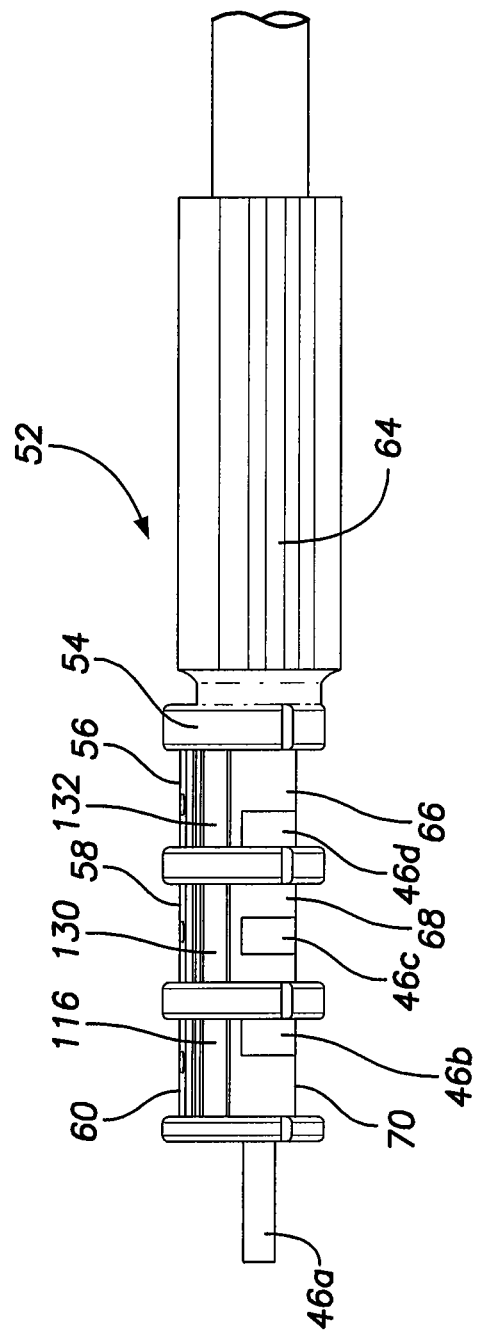
FIG. 9 is a front view of the connector sleeve and lead connector end illustrating full insertion of the lead into the connector sleeve.

The alignment of the ring contacts 46B-46D of the lead connector end 46 with the corresponding contact dimples 116, 118, 130, 131, 132, 133 of the conductive clips 56-60 can be visually verified by the operator through the viewing apertures 66-70 of the housing 54. For example, FIG. 9 is a front view of the connector sleeve 52 and lead connector end 46 illustrating full insertion of the lead connector end into the connector sleeve. As can be seen, a visual verification of the alignment of the contact dimples 116, 118, 130, 131, 132, 133 of the conductive clips 56-60 with the ring contacts 46B-46D of the lead connector end 46 can be accomplished through the viewing apertures 66-70 of the housing 54. In addition, the operator may verify that the proper conductive clips 56-60 reside within the corresponding clip recesses such that each conductive clip engages at least one ring contact 46B-46D on the lead connector end 46. In addition, the slit opening 64 provides for removal of the connector sleeve from the lead connector end without the need of removing the guide wire or stylet from within the lead.

As described above, the electrical connections of the IPG lead can be tested by connecting the lead to the PSA, such as through one or more alligator clips. FIG. 10 is a back isometric view of the connector sleeve 52 with a fully inserted lead connector end 46 and several alligator clips 160 of a PSA for electrically connecting to the connector sleeve. In the embodiment shown, four alligator clips 160 are used to test the electrical connections of the lead. Traditionally, the alligator clips 160 are attached directly to the lead connector end 46 in an attempt to contact the ring contacts of the lead connector end. However, through the use of connector sleeve 52, the alligator clips 160 of the PSA may be applied to the conductive clips 56-60 of the sleeve to test the electrical connections of the IPG lead. In the example shown, an alligator clip 160 is applied to each conductive clip 56-60 of the connector sleeve 52 as well as to the tip conductor 46A of the lead. Through these connections, the placement of the lead within the heart or other location within the body may be tested, without damaging the lead connector end 46 of the lead. The connector sleeve 52 disclosed herein may be employed with any multi-polar lead connector configuration regardless of the number of contacts carried by the lead connector configuration, the design of the connector sleeve simply being modified to increase the number of clips carried by the connector sleeve to correspond to the number of contacts of the lead connector configuration.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. An adapter for testing an implantable medical lead with a testing device and a cable arrangement in communication with the testing device and terminating in pinching clips, the implantable medical lead including a lead connector end with ring contacts, the adapter comprising:
    a housing with a handle portion, a connector interface portion and a bore through the handle portion and the connector interface portion configured to receive the lead connector end of the implantable medical lead;
    conductive clips disposed in respective recesses in the connector interface portion of the housing, the conductive clips configured to electrically connect to the ring contacts of the lead connector end of the implantable medical lead when the lead connector end is positioned within the bore of the housing; and
    insulating walls disposed on the connector interface portion of the housing between the adjacent conductive clips, the insulating walls configured to prevent electrical communication between the conductive clips,
    wherein each conductive clip is configured to directly receive and electrically and mechanically connect with a respective pinching clip of the cable arrangement.

2. The adapter of claim 1, wherein each conductive clip includes a contact dimple, and the contact dimple is configured to make electrical contact with the respective ring contact on the lead connector end when the lead connector end is fully received in the bore of the housing and the respective pinching clip is applied to the conductive clip.

3. The adapter of claim 1, further comprising:
    an alignment stub disposed within at least one of the recesses in the connector interface portion of the housing; and
    wherein at least one of the conductive clips includes an alignment opening configured to engage the alignment stub to align the at least one of the conductive clips within at least one of the recesses in the connector interface portion of the housing.

4. The adapter of claim 1, further comprising:
viewing apertures respectively corresponding to the conductive clips and configured to allow visual verification of the alignment of the conductive clips with respective corresponding ring contacts of the lead connector end when the lead connector end is fully positioned within the bore of the housing.

5. The adapter of claim 1, wherein at least one of the conductive clips further comprises a set of ridges along the surface of the at least one of the conductive clips, the ridges being configured to enhance pinching clip engagement of the of the at least one of the conductive clip.

6. The adapter of claim 1, further comprising:
a bossing feature disposed on at least one of the insulating walls and configured to engage the conductive clip adjacent the at least one of the insulating walls to retain the conductive clip within the recess associated with the conductive clip; and
at least one notch disposed within the recess, the notch configured to engage a punch-in feature of the conductive clip.

7. The adapter of claim 1, further comprising:
an opening along the length of the housing configured allow removal of the adapter from about the lead connector end without necessitating removal of a guide wire or stylet from within the implantable medical lead.

8. The adapter of claim 1, wherein at least one of the insulating walls includes a stepped bore configured to engage the lead connector end of the implantable medical lead when the lead connector end is positioned within the bore of the housing.

9. The adapter of claim 1, wherein the lead connector end conforms to the IS4 or DF4 standard and includes three ring contacts and a pin contact.

10. The adapter of claim 9, wherein the bore of the housing is configured such that the pin contact protrudes from a distal end of the adapter when the lead connector end is fully received in bore.

11. The adapter of claim 1, wherein the conductive clips are configured such that the conductive clips do not make electrical contact with the respective contact rings of the lead connector end of the implantable medical lead when the lead connector end is received in the bore of the housing without the pinching clips being applied to the respective conductive clips.

12. The adapter of claim 11, wherein the pinching clips include alligator clips.

13. A connector interface device for connecting a testing cable to a lead connector end of an implantable medical lead, the lead connector end including ring contacts and the testing cable terminating in pinching clips, the connector interface device comprising:
a housing with a handle portion and conductor positions;
a bore through the handle portion of the housing and configured to receive the lead connector end of the implantable medical lead; and
a conductor clip located at a respective conductor position, each conductor clip configured to electrically connect to a respective ring contact on the lead connector end when the lead connector end is positioned within the bore, and each conductor clip configured to directly receive and electrically and mechanically connect with a respective pinching clip of the testing cable.

14. The connector interface of claim 13, wherein the conductor positions include conductor recesses.

15. The connector interface of claim 14, wherein at least one of the conductor clips includes a u-shaped conductive clip disposed in a respective conductor recess, each conductive clip configured to electrically connect to a respective ring contact on the lead connector end when the lead connector end is positioned within the bore.

16. The connector interface of claim 13, wherein the conductor clip is configured to be electrically connected to a respective ring contact via application of a pinching clip to the conductor member.

17. The connector interface of claim 13, further comprising:
viewing apertures corresponding to the conductor clips and configured to allow visual verification of the alignment of the ring contacts with the corresponding conductor clips when the lead connector end is positioned within the bore of the housing.

18. The connector interface of claim 13, further comprising:
an insulating wall between adjacent conductor clips and configured to prevent electrical communication between the conductor clips.

19. The connector interface of claim 13, wherein the conductor clips are configured such that the conductor clips do not make electrical contact with the respective contact rings of the lead connector end when the lead connector end is received in the bore without the pinching clips being applied to the respective conductor clips.

20. The connector interface of claim 13, further comprising:
an opening along the length of the housing configured allow removal of the connector interface from about the lead connector end without necessitating removal of a guide wire or stylet from within the implantable medical lead.

21. The connector interface of claim 13, wherein at least one of the following is true: the lead connector end conforms to the IS4 standard and includes three ring contacts and a pin contact; or the pinching clips include alligator clips.

22. A method for testing placement of a distal end of an implantable medical lead within a patient, the method comprising:
positioning the distal end of the implantable medical lead at a heart location of the patient;
inserting the lead connector end into a connector interface sleeve, the connector interface sleeve configured to provide conductor clips for a testing cable in communication with a testing device for testing the placement of the distal end of the lead; and
connecting the testing cable to the connector interface sleeve at the conductor clips, each conductor clip of the connector interface sleeve corresponding to a single respective contact ring of the lead connector end, and each conductor clip configured to directly receive and electrically and mechanically connect with a respective pinching clip of the testing cable.

23. The method of claim 22, wherein connecting the testing cable to the connector interface sleeve includes applying a single respective pinching clip of the testing cable to each conductor clip of the connector interface sleeve.

24. The method of claim 23, wherein at least one of the pinching clips includes an alligator clip.

25. The method of claim 23, wherein applying the single respective pinching clip to each conductor clip causes a clip portion of each conductor clip to come into electrical contact with the single respective contact ring of the lead connector end.

26. The method of claim 22 further comprising:
with the lead connector end inserted in the connector interface sleeve, receiving at least one electrical signal from the testing cable at the testing device; and
analyzing the at least one electrical signal at the testing device to determine placement of the distal end of the implantable medical lead.

\* \* \* \* \*